United States Patent
Anderson et al.

(10) Patent No.: US 11,065,031 B2
(45) Date of Patent: Jul. 20, 2021

(54) SYSTEMS AND METHODS FOR ASSEMBLING TISSUE GRAFTS

(71) Applicant: The General Hospital Corporation, Boston, MA (US)

(72) Inventors: Richard Rox Anderson, Boston, MA (US); Joshua Tam, Andover, MA (US); Walfre Franco, Westborough, MA (US); William Farinelli, Danvers, MA (US); Ying Wang, Winchester, MA (US); Martin Purschke, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 156 days.

(21) Appl. No.: 16/344,737

(22) PCT Filed: Oct. 30, 2017

(86) PCT No.: PCT/US2017/059035
§ 371 (c)(1),
(2) Date: Apr. 24, 2019

(87) PCT Pub. No.: WO2018/081707
PCT Pub. Date: May 3, 2018

(65) Prior Publication Data
US 2019/0269430 A1    Sep. 5, 2019

Related U.S. Application Data

(60) Provisional application No. 62/414,405, filed on Oct. 28, 2016, provisional application No. 62/478,207, filed on Mar. 29, 2017.

(51) Int. Cl.
*A61B 17/322*    (2006.01)
*A61L 27/36*    (2006.01)
*A61B 17/00*    (2006.01)

(52) U.S. Cl.
CPC ........ *A61B 17/322* (2013.01); *A61L 27/3691* (2013.01); *A61B 2017/00747* (2013.01);
(Continued)

(58) Field of Classification Search
CPC ........ A61B 17/322; A61B 2017/00747; A61B 2017/00752; A61B 2017/3325; A61B 2017/00969
See application file for complete search history.

(56) References Cited

U.S. PATENT DOCUMENTS 4,418,691 A    12/1983    Yannas
4,773,418 A    9/1988    Hettich
(Continued)

FOREIGN PATENT DOCUMENTS

WO    2016127091 A1    8/2016
WO    2016164890 A1    10/2016

OTHER PUBLICATIONS

International Searching Authority, International Search Report and Written Opinion for application PCT/US2017/059035, dated Jan. 5, 2018, 13 pages.
(Continued)

*Primary Examiner* — Tuan V Nguyen
(74) *Attorney, Agent, or Firm* — Quarles & Brady LLP

(57) ABSTRACT

Systems and methods for assembling a plurality of tissue grafts are provided. A method includes harvesting the plurality of micro tissue grafts from a donor site, arranging the plurality of micro tissue grafts in a desired orientation, forming a tissue construct containing the plurality of micro tissue grafts arranged in the desired orientation, and applying the tissue construct to a recipient site.

18 Claims, 10 Drawing Sheets

(52) U.S. Cl.
CPC ............... *A61B 2017/00969* (2013.01); *A61B 2017/3225* (2013.01)

(56) References Cited

U.S. PATENT DOCUMENTS

| | | |
|---|---|---|
| 9,060,803 B2 | 6/2015 | Anderson |
| 2004/0175690 A1* | 9/2004 | Mishra ................. A61B 17/322 435/1.1 |
| 2011/0313429 A1 | 12/2011 | Anderson |
| 2012/0035618 A1 | 2/2012 | Sabir |
| 2012/0271320 A1 | 10/2012 | Hall |
| 2015/0216545 A1 | 8/2015 | Anderson et al. |
| 2015/0328381 A1 | 11/2015 | Swain et al. |
| 2016/0166732 A1 | 6/2016 | Tumey et al. |
| 2016/0310157 A1* | 10/2016 | Guiles ................ A61B 17/3205 |

OTHER PUBLICATIONS

Kobayashi, N., et al. "Optically transparent ferromagnetic nanogranular films with tunable transmittance." Scientific reports 6 (2016): 34227.

Tam, Joshua, et al. "Fractional skin harvesting: autologous skin grafting without donor-site morbidity." Plastic and Reconstructive Surgery Global Open 1.6 (2013).

Ziolo, Ronald F., et al. "Matrix-mediated synthesis of nanocrystalline ?-Fe2O3: a new optically transparent magnetic material." Science 257.5067 (1992): 219-223.

European Patent Office, Extended European Search Report for application 17864294.8. dated May 7, 2020.

\* cited by examiner

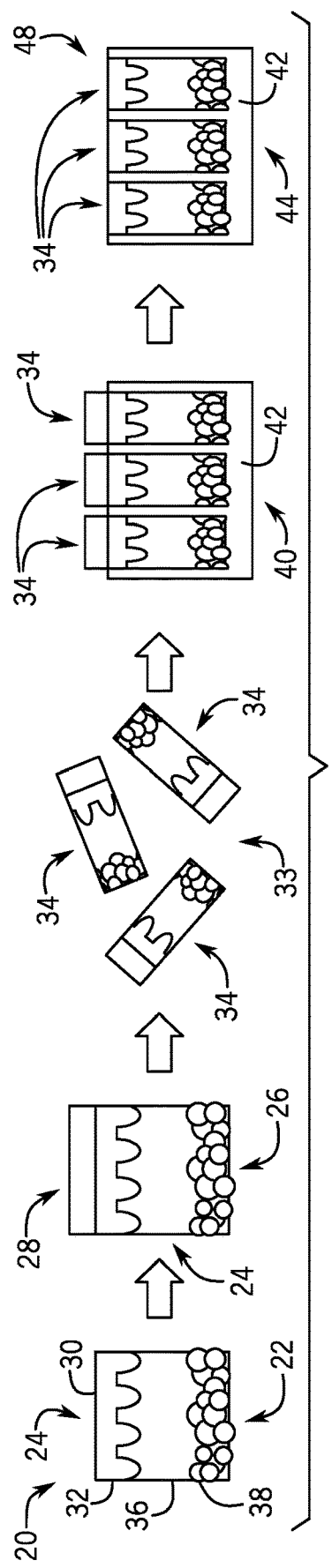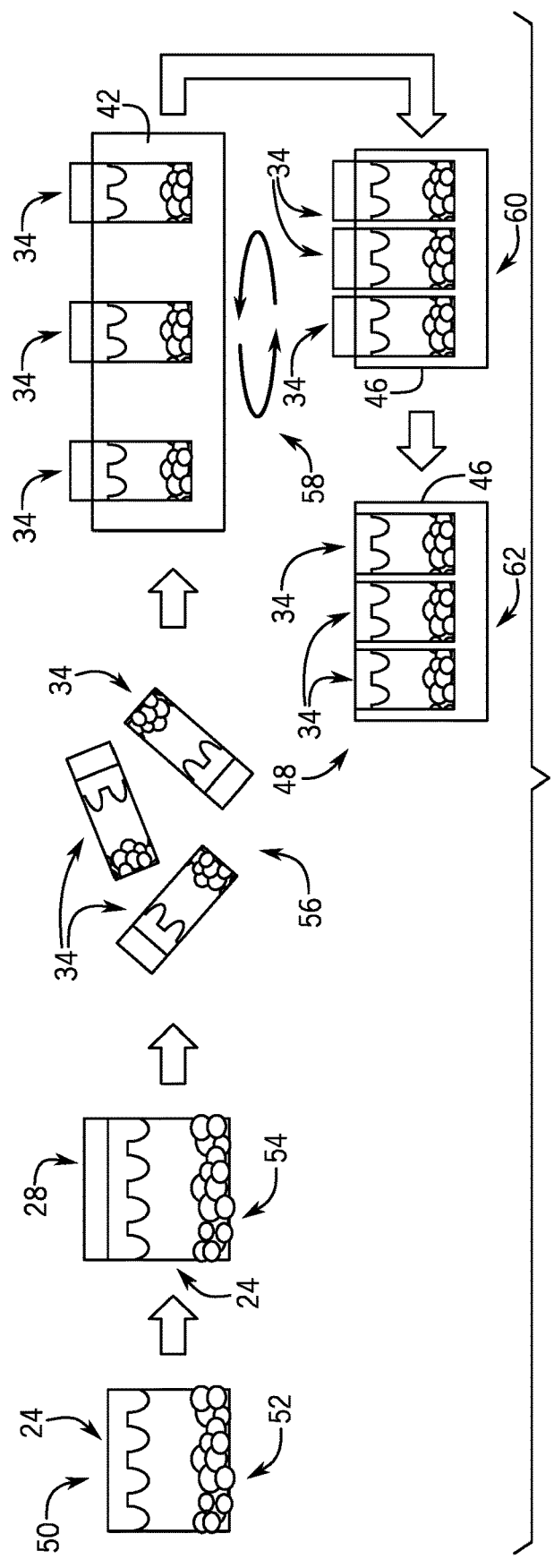

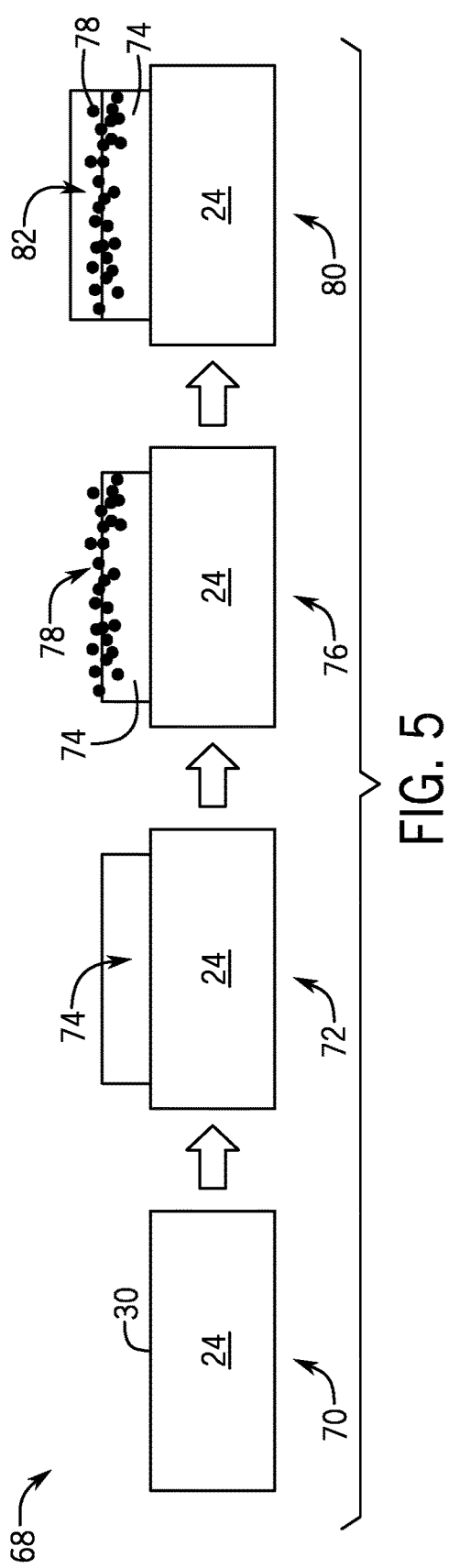
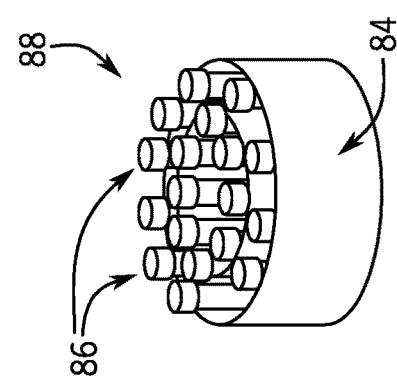
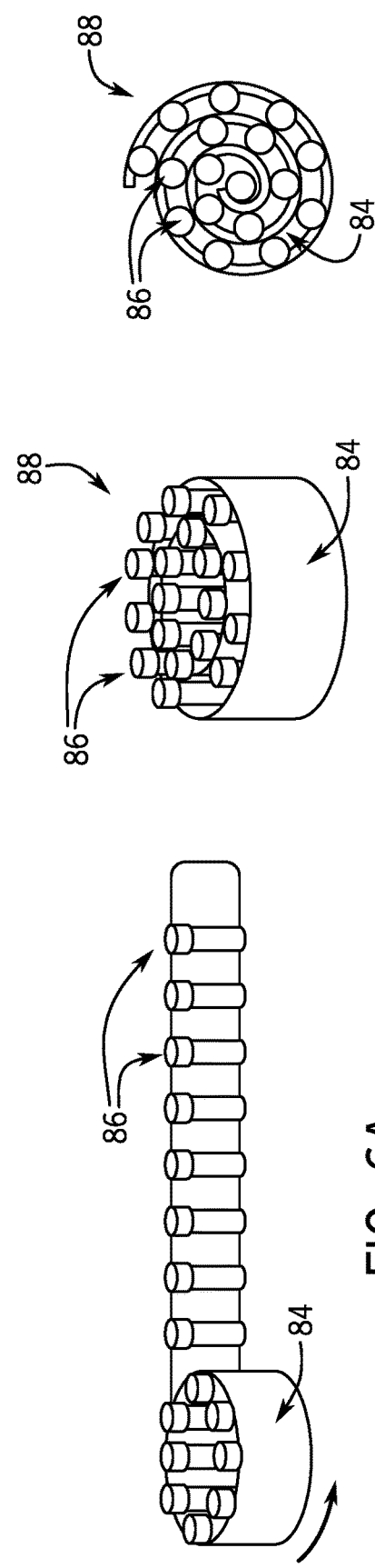
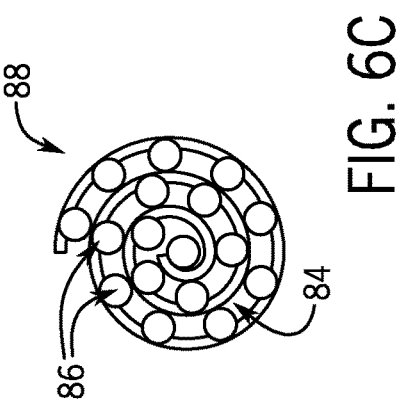

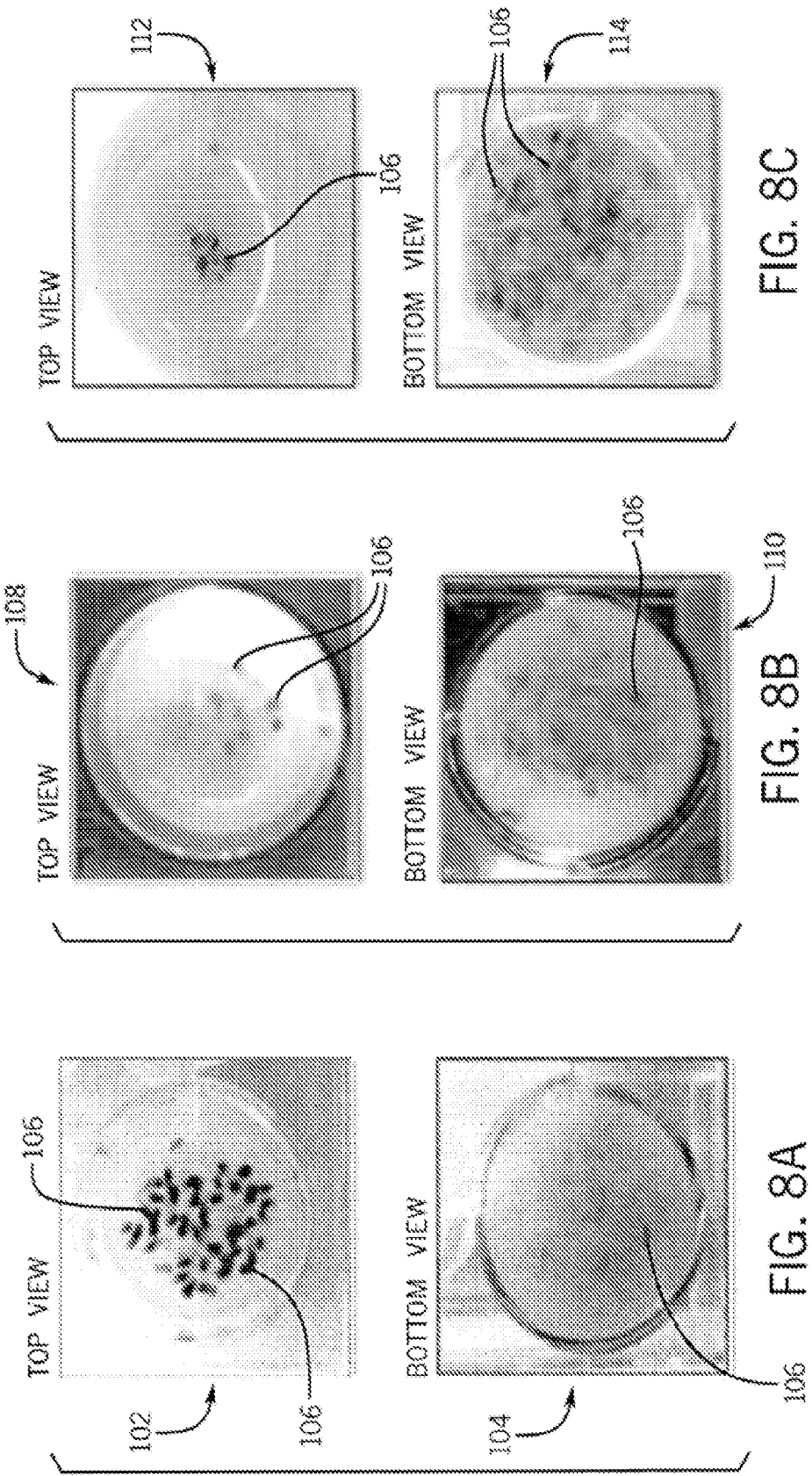

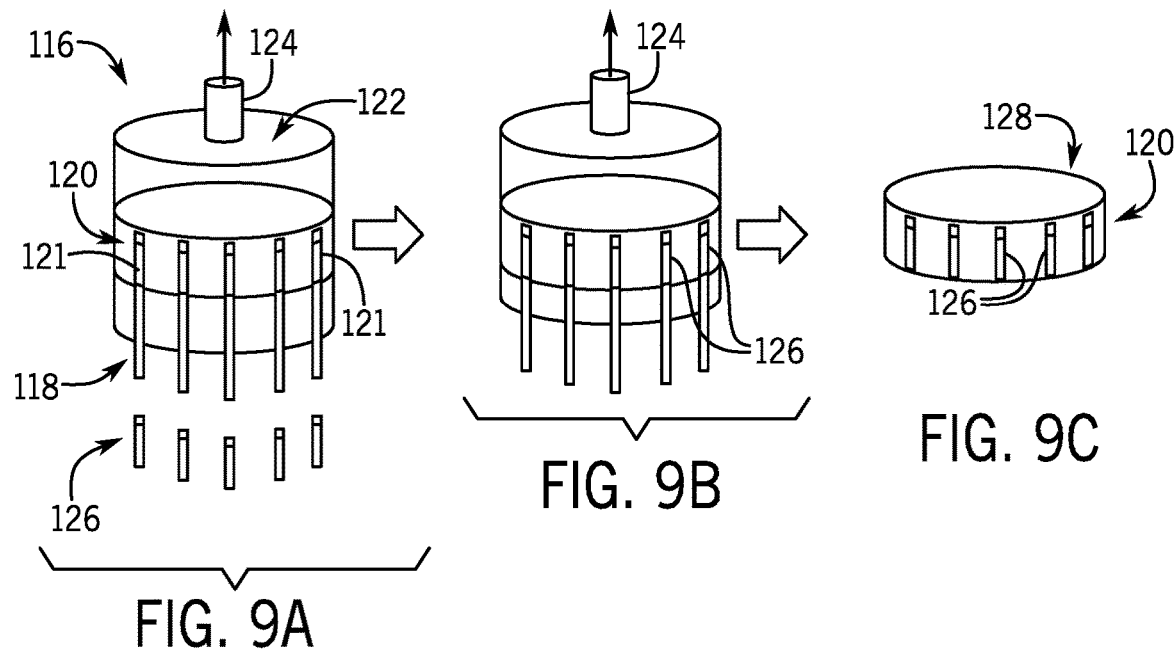
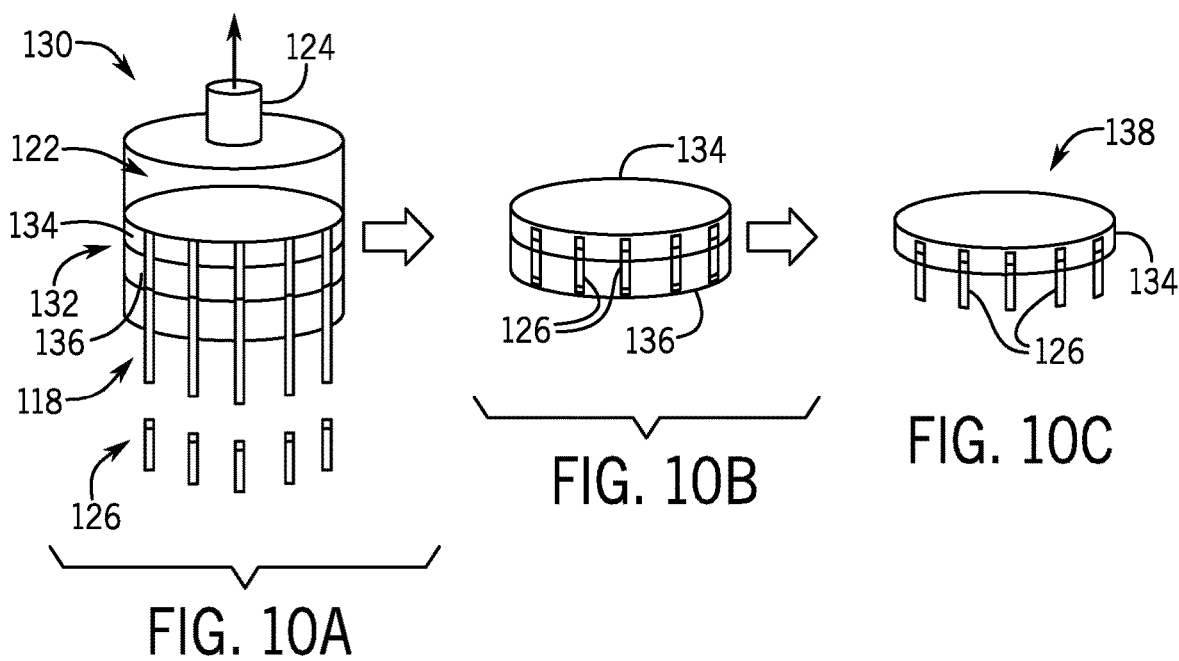

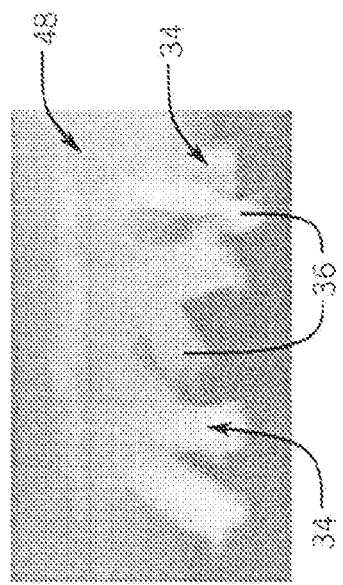
FIG. 11B
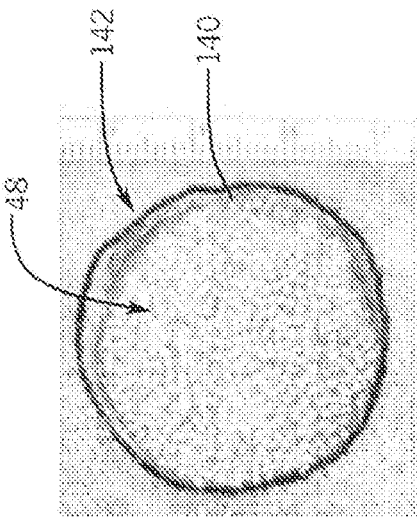
FIG. 12B
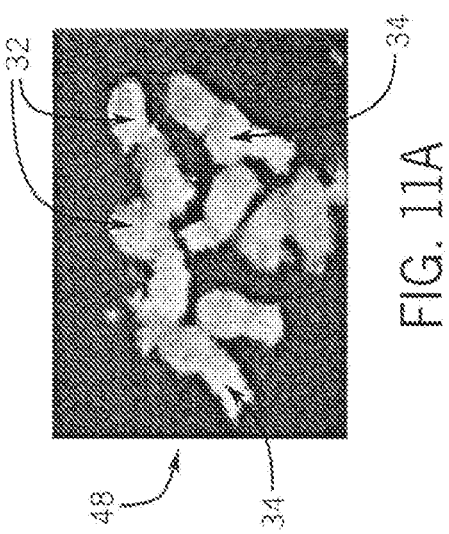
FIG. 11A
FIG. 12A

SYSTEMS AND METHODS FOR ASSEMBLING TISSUE GRAFTS

CROSS-REFERENCE TO RELATED APPLICATIONS

This application represents the national stage entry of PCT International Application No. PCT/US2017/059035 filed Oct. 30, 2017, which is based on, claims priority to, and incorporates herein by reference in its entirety, U.S. Provisional Patent Application Ser. No. 62/414,405, filed on Oct. 28, 2016, and U.S. Provisional Patent Application Ser. No. 62/478,207, filed on Mar. 29, 2017.

STATEMENT REGARDING FEDERALLY FUNDED RESEARCH

This invention was made with government support under W81XWH-13-2-0054 awarded by the Department of Defense. The government has certain rights in the invention.

BACKGROUND

An autograft can refer to tissue transplanted from one part of an individual's body (e.g., a "donor site") to another part (e.g., a "recipient site"). Autografts can be used, for example, to replace missing skin and other tissue and/or to accelerate healing resulting from trauma, wounds, burns, surgery, and birth defects. Generally, grafting procedures can be limited by the amount of tissue that can be removed from the donor site without causing excessive adverse effects. More specifically, availability of tissue for autografting can be limited by a total area of tissue needed, healing behavior of the donor site, similarity of the donor and recipient sites, aesthetic considerations, and/or other characteristics of candidate donor and/or recipient sites.

A sheet graft is one type of autograft and refers to a piece of tissue that is removed, or harvested, from an undamaged donor site. For example, a sheet graft may be obtained using an instrument structured to gently shave a piece of tissue from the skin at the donor site. The size of the donor skin piece used for the graft may be about the same size as the damaged recipient site, slightly larger than the recipient site (e.g., to account for potential shrinkage of the graft tissue after harvesting), or smaller than the recipient site (e.g., with grafts that can be meshed and expanded). Once harvested, the sheet graft can be applied over the recipient site wound, stapled or otherwise fastened in place, and allowed to heal.

Sheet grafts can be full-thickness or split-thickness. For example, a conventional split-thickness graft can be formed by harvesting a sheet of epidermis and upper dermal tissue from a donor site, whereas full-thickness skin grafts can be formed using sheets of tissue that include the entire epidermis layer and a dermal component of variable thickness. The type of sheet graft used can affect healing at both the donor site and the recipient site.

For example, in conventional split-thickness grafts, the skin tissue may grow back at the donor site in a process similar to that of healing a second-degree burn. Split-thickness grafts may thus be preferable to full-thickness grafts because the donor site can at least partially recover on its own, albeit often with scarring, pain, and other long-term side effects. However, skin tissue removed from the donor site for a split-thickness skin autograft generally includes only a thin epithelial layer, which can lack certain elements of the dermis that would improve structural stability and normal appearance at the recipient site once healed.

In conventional full-thickness grafts, more characteristics of normal skin, such as color, texture, and thickness, can be maintained at the recipient site following the grafting procedure (i.e., because the dermal component can be preserved in such grafts). For example, full-thickness grafts can contain a greater collagen content, dermal vascular plexus, and epithelial appendages as compared to split-thickness grafts. Full-thickness grafts may also undergo less contraction while healing. These properties can be important on more visible skin areas, such as the face and hands. Additionally, hair can be more likely to grow from full-thickness grafts than from split-thickness grafts, and sweat glands and sebaceous glands can be more likely to regenerate in full-thickness grafts than in split-thickness grafts, taking on the sweating characteristics of the recipient site.

While full-thickness grafts can provide improved tissue quality at the recipient site, the donor site is completely sacrificed because there is no dermis left for skin to regenerate from. Thus, there is a very limited availability of potential donor sites, and donor sites for full-thickness grafts must be surgically closed. Additionally, full-thickness grafts require more precise conditions for survival because of the greater amount of tissue requiring revascularization. As such, conventional full-thickness skin grafts are generally limited to relatively small, uncontaminated, well-vascularized wounds, and may not be appropriate for as many types of graft procedures as split-thickness grafts.

In light of the above, it may be desirable to provide systems and methods for tissue harvesting and grafting that provide efficient graft tissue with minimal donor site scarring while also properly replicating normal tissue microanatomy at the recipient site. Additionally, it is desirable for such systems and methods to be scalable for use at recipient sites of various sizes and shapes.

SUMMARY

The systems and methods of the present disclosure overcome the above and other drawbacks by providing fractional tissue grafts, in the form of full-thickness micro tissue columns, in a tissue construct that maintains a desired orientation of the individual tissue columns, such as a substantially vertical, epidermal-dermal orientation. Multiple solid tissue constructs can be used as scalable building blocks arranged in a side-by-side manner to properly fit a desired size and geometry of a wound.

In accordance with one aspect of the disclosure, a method for assembling a plurality of micro tissue grafts is provided. The method includes harvesting the plurality of micro tissue grafts from a donor site, arranging the plurality of micro tissue grafts in a desired orientation, forming a tissue construct containing the plurality of micro tissue grafts arranged in the desired orientation, and applying the tissue construct to a recipient site.

In accordance with another aspect of the disclosure, a method for assembling a plurality of micro tissue grafts is provided. The method includes placing an apparatus over a donor site, where the apparatus includes an array of needles, a matrix with holes corresponding to each of the needles in the array, and a mesh over the matrix. The method also includes applying a vacuum over the apparatus to pull the plurality of micro tissue grafts through the array of needles and into the holes of the matrix, where the mesh traps the plurality of micro tissue grafts within the holes, removing the matrix from the mesh and the array of needles to form a tissue construct including the plurality of micro tissue grafts within the matrix, and applying the tissue construct to a recipient site.

In accordance with yet another aspect of the disclosure, an apparatus for assembling a plurality of micro tissue grafts into a tissue construct is provided. The apparatus includes an array of needles, a matrix, and a mesh. The needles of the array are each sized to harvest a respective micro tissue graft from a donor site, and the matrix is positioned over the array of needles. The matrix includes holes configured to receive the micro tissue grafts from the needles. Additionally, the mesh is positioned over the matrix. The mesh is sized to permit air to pass therethrough so that an applied vacuum pulls the micro tissue grafts through the needles into the matrix, and is also sized to contain the micro tissue grafts within the matrix.

The foregoing and other advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2 is a diagram illustrating a hydrophobic coating technique for orienting tissue grafts.

FIG. 3 is a diagram illustrating a hydrophobic coating and orbital motion technique for orienting tissue grafts.

FIGS. 4A-4D illustrate top-down views of tissue grafts and FIG. 4F illustrates an isometric view of a tissue graft.

FIG. 5 is a diagram illustrating a magnetic coating technique for orienting tissue grafts.

FIGS. 6A-6C illustrate a rolling technique for orienting tissue grafts, where FIG. 6A illustrates a side view of a supporting material being rolled with spaced-apart tissue grafts, FIG. 6B illustrates a side view of a rolled tissue construct including a supporting material and oriented tissue grafts, and FIG. 6C illustrates a top view of the rolled tissue construct of FIG. 6B

FIGS. 8A-8C illustrate top and bottom views of tissue grafts with stained epidermal layers, where FIG. 8A illustrates tissue grafts in a solution and oriented according to the hydrophobic coating and orbital motion technique of FIG. 3, FIG. 8B illustrates untreated tissue grafts, and FIG. 8C illustrates tissue grafts in a solution and oriented according to an orbital motion technique.

FIGS. 9A-9C illustrate steps of a combined tissue harvesting and orienting technique using an apparatus including a needle array, a matrix, and a mesh covering.

FIGS. 10A-10C illustrate steps of a combined tissue harvesting and orienting technique using an apparatus including a needle array, a bilayer matrix, and a mesh covering.

FIGS. 11A and 11B illustrate top and side views, respectively, of tissue grafts in a construct.

FIGS. 12A and 12B illustrate top views of a construct including oriented tissue grafts, where FIG. 12A illustrates an assembled construct and FIG. 12B illustrates the construct applied to a wound.

FIG. 13A illustrates the wound at time zero, FIG. 13B illustrates the wound two weeks after time zero, and FIG. 13C illustrates the wound six weeks after time zero.

FIGS. 14A-140C illustrate top views of a wound healed by randomly oriented micro tissue grafts, where FIG. 14A illustrates the wound at time zero.

FIG. 15A illustrates the wound at time zero, FIG. 15B illustrates the wound one week after time zero, FIG. 15C illustrates the wound three weeks after time zero, FIG. 15D illustrates the wound four weeks after time zero, FIG. 15E illustrates the wound six weeks after time zero, and FIG. 15F illustrates the wound eight weeks after time zero.

DETAILED DESCRIPTION

The disclosure provides systems and methods for organizing and assembling tissue grafts. More specifically, the present systems and methods enable assembling multiple micro tissue grafts, in the form of biological micro tissue columns, into a larger tissue construct in a way that maintains a desired orientation of the individual tissue columns.

For example, full-thickness skin tissue can be harvested from a donor site in the form of small columns (e.g., several hundred micrometers in diameter) without causing scarring at the donor site. These micro tissue columns can be applied to wound beds as "random" fractional grafts to improve wound healing. However, because skin is naturally polarized in architecture, engrafting micro tissue columns as an array having a proper epidermal-dermal orientation into the wound bed can further improve healing by accelerating re-epithelialization processing, recapitulating normal dermal architecture, and reducing scarring. As such, the methods and systems disclosed herein facilitate the orientation of micro tissue columns, and enable their assembly into three-dimensional, full-thickness constructs. The present systems and methods also provide a practical, scalable solution for using large numbers of micro tissue columns to improve healing wounds of various sizes and shapes.

Figure 1:
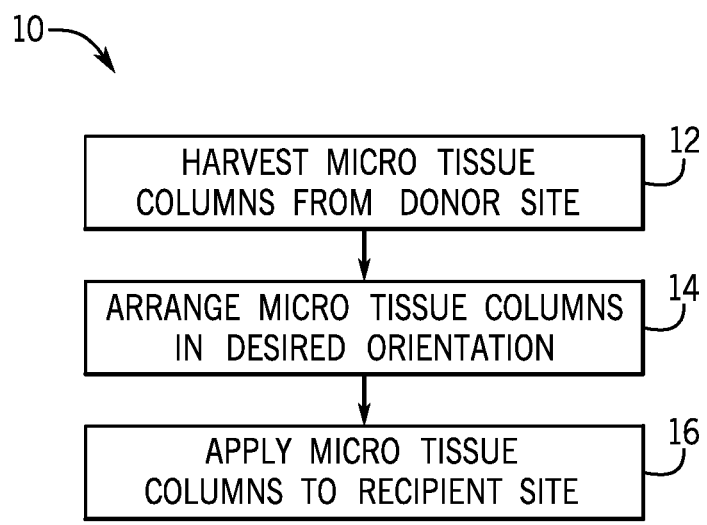
FIG. 1 is a flow diagram illustrating a method for organizing and assembling tissue grafts.

FIG. 1 illustrates a method 10 for assembling micro tissue columns (MTCs) in accordance with the present disclosure. Generally, as shown in FIG. 1, MTCs are harvested from a donor site at step 12. At step 14, some or all MTCs are arranged in a desired orientation (e.g., matching an epidermal-dermal polarity of normal skin). And at step 16, the oriented MTCs are applied to a recipient site. While the term micro tissue columns, or MTCs, is used herein, it should be noted that this term may be interchangeable with micro tissue grafts or micrografts. Furthermore, when the subject tissue is skin, MTCs may be referred to as micro skin tissue columns (MSTCs).

Referring now to step 12, the MTCs can be harvested from a donor site. More specifically, MTCs can be formed by removing elongated, substantially cylindrical portions of tissue from the donor site, thus leaving holes therein. In some embodiments, a diameter or width of an MTC can be less than about 2 millimeters (mm) or less than about 1 mm. In some embodiments, the diameter or width can be less than about 0.5 mm, less than about 0.3 mm, or about 0.2 mm. In further embodiments, the diameter or width can be between about 0.8 mm and 0.3 mm. In other embodiments, the diameter or width can be between about 0.7 mm and 0.2 mm.

Each MTC can be a full-thickness graft, including both epidermal tissue and dermal tissue from the donor site. In general, it can be preferable to harvest MTCs with epidermal tissue and dermal tissue, while avoiding a significant amount of subcutaneous tissue or muscle tissue (though, in some applications, MTCs can include subcutaneous tissue and/or muscle tissue). For example, each MTC can be about 3 mm in height, which can correspond to a total depth of a typical skin layer (e.g., including both epidermal and dermal layers, where the dermal layer includes hair follicles and sweat or sebaceous glands). A different height may be used, such as between about 2 mm and about 4 mm, based on the particular skin or tissue characteristics of the donor site. Additionally, MTCs can include stem cells throughout the dermal tissue (e.g., stem cells associated with hair follicles and sweat glands and/or stem cells in a lower portion of the dermal layer, for example, near a dermal/fatty layer boundary).

Generally, the MTCs can be harvested from the donor site in a way that minimizes or prevents scarring at the donor site. For example, a size of a donor site hole created by a respective MTC can be selected so that the minor damage created heals rapidly and/or without scarring. More specifically, each donor site hole can be small enough to heal quickly by regeneration, that is, by replacement of the harvested tissue volume with new skin tissue that is normal in both structure and function, without or with minimal scarring. Additionally, the size of the donor site holes created by the MTCs can be selected based on creating portions of tissue that can be small enough to promote viability when transplanted or placed in a growth medium, and large enough to form a sufficient amount of graft tissue and/or to capture tissue structures that may be present in the donor tissue.

In some embodiments, a fraction of surface tissue removed from the donor site (which can correspond to a fractional surface area of the donor site occupied by the holes) can be less than about 70%, less than or equal to about 50%, or more preferably between about 10% and about 30%. The fraction of tissue removed can be sufficiently large to provide enough harvested MTCs to form an appropriately sized graft, but small enough to facilitate rapid healing at the donor site based on growth from the remaining undamaged tissue. Other fractions of tissue can be removed from a donor site depending on factors such as, for example, the particular characteristics of the donor site, the size of the graft needed, and the overall amount of donor site tissue available.

According to some embodiments, the MTCs can be harvested using one or more harvesting needles, such as, for example, 19-gauge coring needles. Furthermore, in some embodiments, the MTCs may be harvested using one or more double-pointed hypodermic needles. However, needles of different types or sizes, individually or grouped in arrays, may be contemplated within the scope of this disclosure. For example, MTCs may be harvested using any of the tools and methods described in U.S. Pat. No. 9,060,803, the entire contents of which is incorporated herein by reference.

The result of step 12 is a fractional skin graft that includes a plurality of harvested MTCs. As described above, rather than a single, large donor site wound, the fractional skin grafting techniques described above create minor donor site wounds that can heal with minimal to no scarring. Additionally, in some embodiments, step 12 can include pretreating the donor site prior to harvesting the MTCs to assist MTC orientation at step 14, as further described below.

Referring now to step 14, the harvested MTCs are assembled in a desired orientation, for example, matching an epidermal-dermal polarity of normal skin. More specifically, at step 14, the MTCs can be assembled into a three-dimensional, full-thickness construct maintaining proper epidermal-dermal, substantially vertical orientation. Step 14 can be accomplished via a self-assembly approach by coating the surface of each tissue column with a substance that induces all, or most, columns to organize in the desired orientation either spontaneously (e.g., by a hydrophobic coating that would float to the top of an aqueous medium) and/or using external factors (e.g., by an external magnet that causes a coating to orient along magnetic field lines, or by controlled agitation or fluid flow). In addition or alternatively, supportive biomaterials can help maintain the overall structure and desired orientation of the assembled tissue columns, forming a construct. These supportive materials can be applied in different ways, such as, for example, first introduced in liquid form then induced to solidify around the assembled tissue columns, or used in solid form and combined with tissue columns in layers or rolls.

Accordingly, in some embodiments, a coating is used to orient MTCs. For example, a surface of the donor site is coated with a coating prior to graft harvesting at step 12. The coating may be a hydrophobic coating, a hydrophilic coating, or any type of coating that exhibits a phase separation in a solution. The coating can be non-toxic and/or biologically inert and, in some applications, silicone-based. Once coated, the MTCs can be extracted and submerged in a solution that causes the MTCs to align in an epidermal-dermal orientation. More specifically, due to the properties of the coating, the coated epidermis of some or all MTCs will spontaneously align in the solution, orienting itself toward the top of the solution.

FIG. 2 illustrates an example coating technique 20. As shown in FIG. 2, at step 22, a donor site 24 can be selected. At step 26, a hydrophobic coating 28, such as petroleum jelly or another suitable coating, can be applied to a surface 30 of the donor site 24 (for example, over an epidermal layer 32 of the donor site). At step 33, MTCs 34 are harvested from the donor site 24 in accordance with step 12 described above. For example, the MTCs 34 can be full-thickness grafts, including the epidermal layer 32 as well as a dermal layer 36 and, optionally, a portion of a dermal/fatty layer boundary 38. At step 40, the MTCs 34 are placed in a solution 42 (for example, in a well plate). Due to the hydrophobic properties of the coating 28, the coated epidermis 32 of some or all MTCs 34 will generally align vertically within the solution 42 in an epidermal-dermal orientation. At step 44, the solution 42 (or a different solution) is induced to solidify around the assembled MTCs 34 to create a construct 48 of oriented MTCs 34. In some embodiments, the solution 42 can be saline or another suitable solution, such as a biocompatible and/or biodegradable polymer capable of solidifying after a time period (e.g., the polymer can solidify a time period after being mixed), or in response to induction (e.g., through application of a cross-linking agent). Additionally, in some embodiments, a different solution may be used at step 44. For example, this other solution may be a supportive biomaterial, such as a biocompatible matrix or collagen solution capable of solidifying after incubation. While the coating 28 may be washed off after alignment in some applications, it may not be necessary in other applications (e.g., the coating 28 may remain on the donor site 24 after would application and be allowed to slough off during the natural turnover of the epidermis).

In some embodiments, the above coating technique may be combined with an agitation step. For example, agitation can help stir MTCs that may have sunk down into the solution, increasing their chances of floating up to the fluid surface. Once at the fluid surface, the hydrophobic coating would cause the MTCs to stay in the desired orientation. Additionally, agitation can increase the likelihood that MTCs floating at the surface will get close enough to each other to cluster together (i.e., due to the effects of surface tension around small floating objects, also known as the "Cheerios effect").

For example, FIG. 3 illustrates a coating and orbital motion technique 50. As shown in FIG. 3, a donor site 24 is selected and coated with a hydrophobic coating 28 at steps 52 and 54, respectively, and coated MTCs 34 are harvested at step 56. Steps 52-56 of FIG. 3 can be generally equivalent to above-described steps 22, 26, and 34 of FIG. 2. Following step 56, however, the harvested and submerged MTCs 34 can be submerged in a solution 42 and agitated to enhance clustering of the MTCs 34 toward each other (e.g., toward the center of the well plate) at step 58. Such agitation can be accomplished, for example, by applying orbital motion using an orbital shaker (not shown). In one specific application, agitation can be accomplished using an orbital shaker at 150 rotations per minute (RPM) for about thirty seconds; however, other orbital shaker parameters may be used in other applications. Additionally, at step 60, the epidermal-dermal oriented MTCs 34 can be placed in a supportive biocompatible material 46. For example, the epidermal-dermal oriented MTCs can be transferred to a new culture plate containing the supportive biomaterial 34, such as a liquid collagen solution or other biocompatible matrix, and again subjected to orbital motion (for example, using an orbital shaker at 200 RPM for about thirty seconds or at other RPM and timing parameters). At step 62, the collagen solution 46, including properly oriented MTCs 34, can be induced to form a solid construct 48. For example, in one application, the collagen solution 46 can be incubated at 37 degrees Celsius for about forty-five minutes to form the solid construct 48.

Figure 4A:
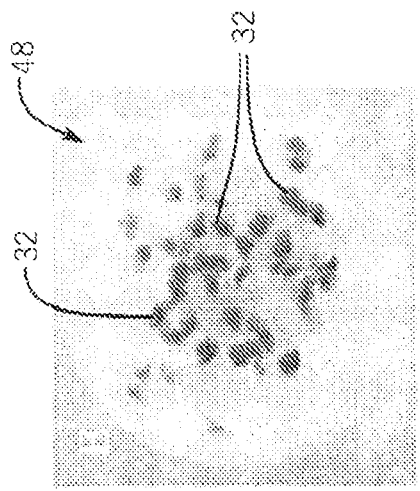
FIGS. 4A-4F are views of tissue grafts in a solution at various steps of the technique illustrated in FIG. 3, where
Figure 4B:
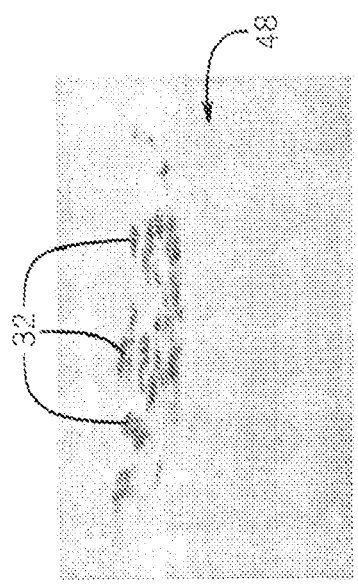
Figure 4C:
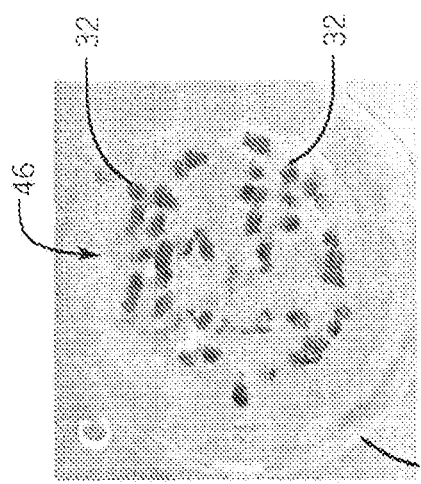
Figure 4D:
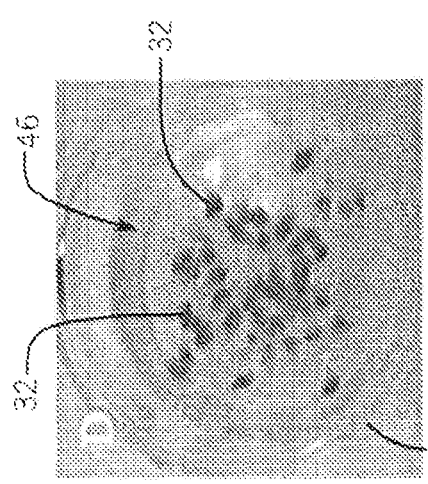
Figure 4E:
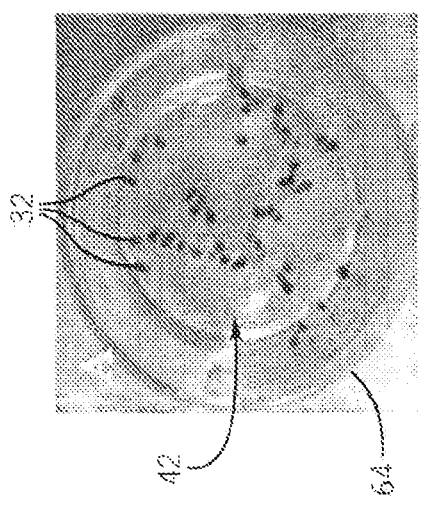
Figure 4F:
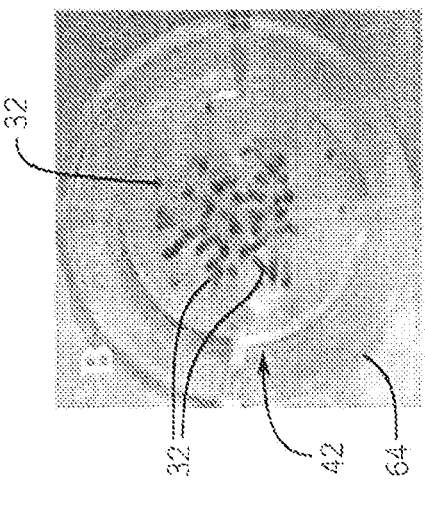

FIGS. 4A-4F illustrate MTCs 34 in accordance with the above technique of FIG. 3, where the epidermis 32 of the donor site was stained with ink before MTC harvesting to illustrate orientation. FIG. 4A illustrates the MTCs 34 coated with a hydrophobic coating and floating in a solution 42 in a well plate 64 with some epidermal layers 32 oriented upward (e.g., corresponding to step 40 above). FIG. 4B illustrates the MTCs 34 (shown by their stained epidermal layers 32) clustered toward the center of the well plate 64 after orbital motion was applied (e.g., corresponding to step 58 above). FIGS. 4C and 4D illustrate the MTCs 34 transferred to a new culture plate 66 in a collagen solution 46 before and after orbital motion, respectively (e.g., corresponding to step 60 above). Accordingly, FIG. 4D illustrates the MTCs 34 clustered toward the center of the well plate 66 after orbital motion was applied. FIGS. 4E and 4F illustrate top and isometric views, respectively, of the MTCs 34 correctly oriented in a solidified fractional skin graft construct 48 (e.g., corresponding to step 62 above, where the collagen solution 46 was induced to solidify).

While the above-described orbital motion may be used to orient MTCs in some embodiments, other types of agitation or fluid flow may be used in other embodiments. For example, in one embodiment, harvested MTCs be routed from the harvesting needles through microfluidic channels or flow channels having a tapered geometry (not shown) in order to maintain their epidermal-dermal orientation from extraction. The channels may also be oriented in a way to facilitate a closer grouping between MTCs. That is, the channels may be oriented to decrease a spacing between MTCs compared to their original spacing when extracted from the donor site. From these channels, the epidermal-dermal oriented MTCs may be transferred to a culture plate containing a biocompatible matrix (such as a collagen solution) and incubated to form a solid construct. In some embodiments, these additional agitation and fluid flow examples may also be combined with any of the coating techniques described herein.

Additionally, in other embodiments, a magnetic or ferromagnetic coating is used to orient MTCs. In this example, a surface of a donor site can be coated with the coating prior to graft harvesting, such as with a magnetic paint or iron oxide particles. The MTCs are then extracted and submerged in a solution (such as saline, a biocompatible matrix, a collagen solution, or another supportive biomaterial), and an external magnet can be used to orient the MTCs within the solution. Due to the magnetic properties of the coating, the coated epidermis of some or all MTCs will align according to magnetic field lines created by the magnet, thus orienting itself toward the top of the solution. Accordingly, the external magnet can be used to control patterning of the MTCs very precisely. Additionally, in some applications, an array of magnets (that is, rather than a single magnet) can be used, for example, to create regions of different patterns or different densities of MTCs within the same tissue construct.

FIG. 5 illustrates an example partial coating technique 68. As shown in FIG. 5, at step 70, a donor site 24 can be selected. At step 72, an adhesive coating 74, such as ostomy glue or another suitable adhesive, can be applied to a surface 30 of the donor site 24. At step 76, iron oxide particles 78 are applied to the adhesive. At step 80, an additional coating 82, such as a spray-on bandage, is applied over the iron oxide particles 78. While not shown in FIG. 5, following step 80, MTCs can be harvested from the donor site (e.g., as described above in accordance with step 12) and placed in a solution. An external magnet can then be positioned over the solution so that some or all MTCs generally align vertically within the solution in an epidermal-dermal orientation. That is, due to the magnetic properties of the coating, the coated epidermis of some or all MTCs will align according to magnetic field lines created by the magnet, orienting itself toward the top of the solution. The solution is then induced to solidify around the assembled MTCs to create a construct of oriented MTCs.

As described above, supportive biomaterials (such as a collagen solution or biocompatible matrix) are used to orient the MTCs and/or maintain MTC orientation in a construct. More specifically, the above-described supportive materials can be used to create a construct that maintains the overall structure and orientation of the assembled tissue columns. As a result, these constructs create a more easily handled graft and, in some applications, can allow for physicians to add drugs, other components, or other cell types as needed.

Accordingly, in line with the above-described techniques, MTCs can be introduced into a supportive material in liquid form, and then the material can be induced to solidify around the tissue columns (for example, by incubation or other suitable techniques).

In other embodiments, however, supportive biocompatible materials can be used in solid form and combined with MTCs in layers or rolls. For example, a supportive material may be used with a rolling technique that preserves the orientation of the MTCs. More specifically, as shown in FIG. 6A, a supportive material 84 (such as a matrix or other type of biomaterial strip) can be rolled up while oriented MTCs 86 are placed onto the material 84 at spaced-apart intervals. This rolling technique can result in a construct 88 having a jelly roll arrangement, as shown in FIGS. 6B and 6C. The size of the construct 88 can be made smaller or larger (e.g., by less or more rolling) according to a desired wound diameter and/or shape. In some embodiments, a rolling device (not shown) can be used to support the supportive material 84 in a substantially vertical orientation while allowing an operator to place the MTCs 86 at predetermined distances from each other onto the supportive material 84 as the rolling device rolls up the supportive material 84. Alternatively, a pick and place gantry machine (not shown) can be used to automatically place MTCs 86 against a vertically positioned strip of matrix material 84 that would roll along as the MTCs 86 were placed on it.

While the above examples include creating a construct having MTCs in supportive materials, in some embodiments, constructs include MTCs formed together (in the desired orientation) in another manner. As such, these constructs can include MTCs that are oriented properly, but not supported by exogenous materials dispersed between MTCs. Accordingly, in some embodiments, a solid construct may be formed by a material or tool that maintains MTCs arranged and oriented by contacting or communicating with an upper surface of the MTCs. For example, after orienting MTCs, an adhesive dressing can be applied to the epidermal surface to "pick up" all of the oriented MTCs as a solid construct. In another example, MTCs can be coated with a magnetic layer, as described above, and then a magnet can be used to pick up all of the oriented MTCs as a solid construct. In these applications, once the oriented MTCs are picked up, thus forming the construct, the construct may be directly applied to a recipient site (as further described below with respect to step 16).

Figure 7:
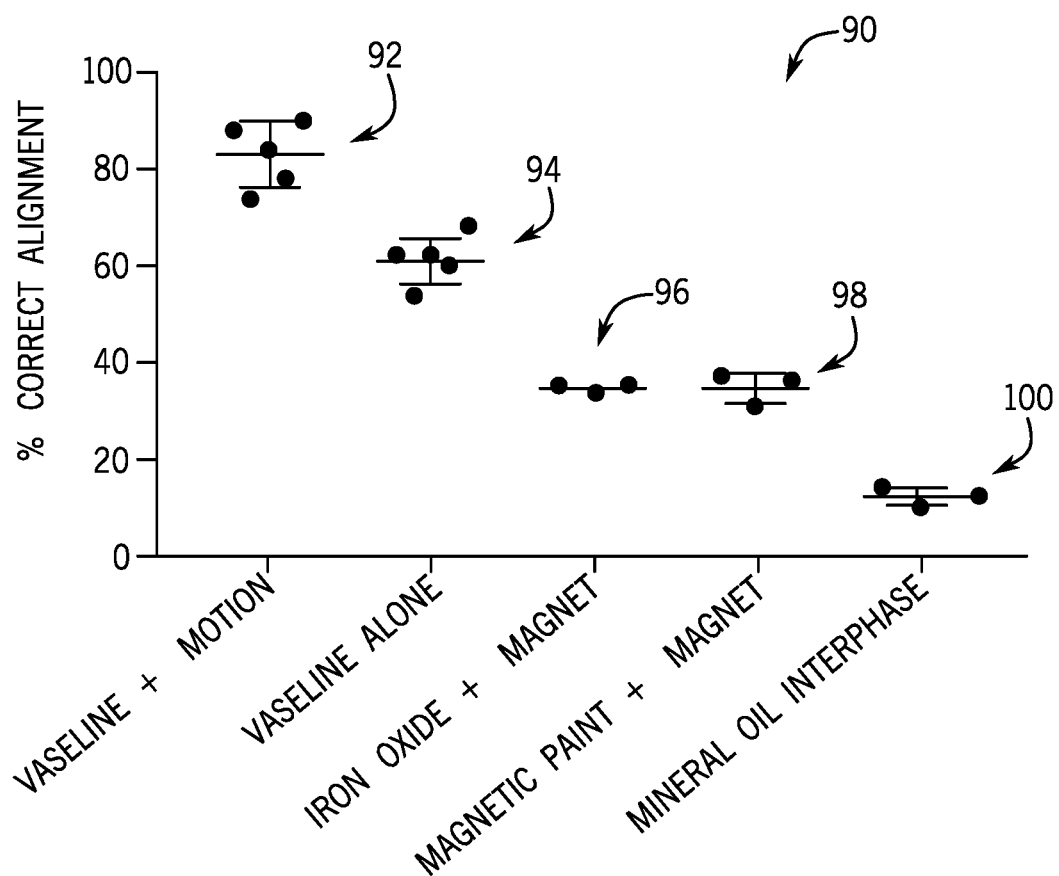
FIG. 7 is a chart illustrating a percentage of correctly aligned tissue grafts when assembled according to different orienting techniques.

In some embodiments, one or more of the above examples may be combined or fully or partially interchanged in order to orient MTCs. In some applications, combining techniques can increase an amount of properly oriented MTCs. For example, FIG. 7 provides a chart 90 illustrating a percentage of correctly aligned MTCs when assembled using: hydrophobic coating plus orbital motion 92 (resulting in about 80%-90% correctly aligned); hydrophobic coating alone 94 (resulting in about 55%-65% correctly aligned); iron oxide with an external magnet 96 (resulting in about 35% correctly aligned); magnetic paint with an external magnet 98 (resulting in about 30%-40% correctly aligned); and a mineral oil interphase 100 (resulting in about 10%-15% correctly aligned). The mineral oil interphase included a mixture of aqueous fluid (e.g., normal saline) and organic fluid (e.g., mineral oil). This interphase can cause MTCs to orient accordingly as the mixture separated into layers (or phases) because MTCs naturally consist of a mostly hydrophilic portion (i.e., the dermis), sandwiched between two hydrophobic portions (i.e., the epidermis on one end, and the subcutaneous fat on the other).

As shown in FIG. 7, using a hydrophobic coating plus orbital motion (in accordance with the technique of FIG. 3) significantly increases the percentage of correctly aligned MTCs compared to the other methods shown. To further illustrate these results, FIG. 8A illustrates top and bottom views 102, 104 of culture plates including MTCs 106, with a stained epidermis, treated with hydrophobic coating and orbital motion. FIG. 8B illustrates top and bottom views 108, 110 of culture plates including untreated MTCs 106 (that is, no hydrophobic coating and no orbital motion), and FIG. 8C illustrates top and bottom views 112, 114 of culture plates including MTCs 106 treated only with orbital motion. As shown in FIGS. 8A-8C, significantly more of the MTCs 106 treated with hydrophobic coating and orbital motion are oriented with their epidermis upward (as shown by the plurality of stained epidermises in the top view of FIG. 8A) compared to the MTCs 106 shown in FIGS. 8B and 8C. However, as noted above, the techniques disclosed herein are not mutually exclusive and one or more techniques may be combined or fully or partially interchanged to further increase the total percentage of correctly aligned MTCs and/or achieve desired characteristics. For example, in one application, magnetic particles may be applied to a hydrophobic coating to provide a high amount of properly oriented MTCs (that is, caused by the hydrophobic coating technique) as well as the capability to create precise patterns of MTCs (that is, using the magnetic techniques).

The above techniques orient MTCs, spontaneously and/or using external factors, after they have been harvested at step 12. However, in some embodiments, steps 12 and 14 may be combined so that MTC harvesting and orienting are completed in a single step. For example, as shown in FIG. 9A, a harvesting and assembling apparatus 116 can include an array of coring needles 118, a pre-molded matrix 120, and a mesh material 122. The array of coring needles 118 may be sized and arranged to harvest MTCs from a donor site, and the matrix 120 may be arranged over the array of coring needles 118 and include a plurality of holes 121, where each hole is aligned with a respective coring needle 118 and includes a diameter substantially equal to an inner diameter of the coring needle 118. The mesh material 122 can be arranged over the matrix 120, for example, to act as a covering over the matrix holes 121 while still permitting suction therethrough.

In operation, as shown in FIG. 9A, the coring needles 118 are placed into the donor site tissue and a vacuum 124 is applied from above the mesh 122 to pull MTCs 126 through the coring needles 118 and into the matrix 120. As shown in FIG. 9B, the mesh material 122 can trap the MTCs 126 within the matrix 120 while still allowing a vacuum to pass through the mesh material 122. As a result, the MTCs 126 remain in the matrix 120 and are correctly aligned in the proper epidermal-dermal orientation. The matrix material 120 can then be removed from the needle array 118 and the mesh material 122, as shown in FIG. 9C, resulting in a tissue construct 128. In other words, the matrix material 120 acts as a supportive biomaterial that maintains the overall structure and desired orientation of the assembled MTCs 126. Accordingly, the matrix material 120 may be biocompatible so that the entire matrix construct 128 may be placed directly into a wound (in accordance with step 16, as further described below). Example biocompatible matrices include, but are not limited to, decellularized tissue (e.g., skin, gut, amnion, or other tissue that has been processed to remove all living cells, so all that's left of the original tissue are the extracellular components), matrices made from natural biomolecules (collagen, fibrin, hyaluronan, etc., used alone or in combination) in various forms (e.g. in a gel or spun into fibers), synthetic materials that are biodegradable and have certain bio-mimicking properties (e.g., biodegradable polymers functionalized with cell adhesion moieties), matrices including collagen, hydrogels, fibrin gels, or carbon scaffolds. Additionally, any of the above examples can include growth factor and/or oxygen concentration enhancing material (e.g., $CaO_2$) and/or other substances.

Furthermore, in some embodiments, as shown in FIGS. 10A-10C, a harvesting and assembling apparatus 130 can include bilayer matrix 132, including an upper layer 134 and a lower layer 136. In such embodiments, suction can be applied to pull the MTCs 126 from a donor site into the bilayer matrix 132, as shown in FIG. 10A, resulting in the MTCs 126 being trapped in the bilayer matrix 132, as shown in FIG. 10B. The needle array 118, the mesh material 122, and one of the matrix layers (such as the lower layer 136) can then be removed. As a result, the MTCs 126 remain in the upper layer 134, in their proper epidermal-dermal orientation with the lower end of each dermis exposed, to form a construct 138, as shown in FIG. 10O. This type of construct, when applied to a wound (as further described below), permits the exposed dermal layer to come into direct contact with the wound bed, which may increase the likelihood of successful re-establishment of blood flow from the wound bed to the MTCs (which can be important for long-term tissue survival).

Referring back to the method of FIG. 2, once MTCs are harvested and oriented at steps 12 and 14 in accordance with any of the above-described techniques, they are applied to a recipient site (such as a wound) at step 16. More specifically, following steps 12 and 14, one or more three-dimensional, full-thickness constructs 48 (or 88, 128, 138) are available for wound healing, and these constructs include MTCs 34 (or 86, 106, 126) in substantially vertical, epidermal-dermal orientation as shown in FIGS. 11A and 11B. These constructs are three-dimensional because they have a usable width, length, and height and are full-thickness because they include epidermal and dermal layers 32, 36 (as shown in FIGS. 11A and 11B). In some embodiments, as shown in FIG. 12A, a construct 48 may be round. However, in other embodiments, constructs may be rectangular, square, or another suitable shape.

According to step 16, the MTCs 34 can be placed in or on a wound in order to entirely, or at least partially, cover the wound. In some embodiments, a single construct 48 may entirely cover a wound 140 at a recipient site 142, as shown in FIG. 12B. In other embodiments, multiple constructs, each containing a plurality of MTCs, can be arranged side-by-side in order to fit the geometry of a wound. For example, a single MTC roll construct 88 (e.g., formed by the rolling technique described above) can fit the geometry of a wound. Alternatively, multiple MTC roll constructs 88 can be arranged side-by-side to fit the geometry of a wound. Accordingly, the present methods can be scalable for use in large and/or asymmetrical wounds by providing one or more solid constructs, each formed with a plurality of MTCs, to be arranged side-by-side at a recipient site.

In light of the above, the present methods allow for assembling multiple MTCs, in a desired orientation, into solid, three-dimensional tissue constructs. Furthermore, one or more systems may be provided to fully or partially execute the above-described methods. When such constructs are applied to a recipient site, the full-thickness MTCs can grow, complete with sweat glands and other complex features of the harvested tissue. Accordingly, these MTCs can be used to assist and improve tissue healing at the recipient site (such as a wound). More specifically, properly oriented MTCs can improve healing by accelerating re-epithelialization processing, recapitulating normal dermal architecture, and/or reducing scarring, as compared to healed untreated wounds and healed wounds treated with randomly oriented MTCs.

In particular, while harvested MTCs can be applied to wound beds randomly, that is, without maintaining the normal epidermal-dermal polarity of skin, MTCs organized in a defined epidermal-dermal orientation can be advantageous to accelerate wound healing by providing for more efficient cell and tissue growth and more faithful replication of normal tissue microanatomy (for example, complex structures in full-thickness tissue grafts, like hair follicles, have defined polarities and are generally less tolerant of being implanted in the wrong orientation). Thus, while randomly oriented MTCs have been shown to improve healing compared to untreated wounds (e.g., by healing faster with less contraction), MTCs assembled and oriented in accordance with the systems and methods described above can further improve healing time, contractile response, skin appearance, and/or structural organization.

Figure 13A:
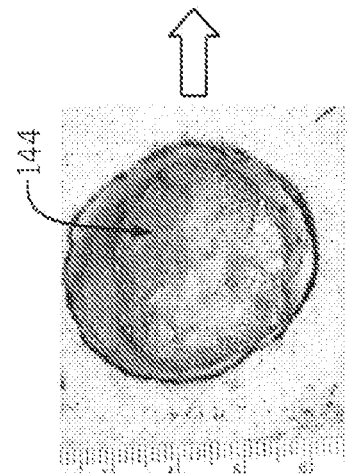
FIGS. 13A-13C illustrate top views of a wound healed by secondary intention, where
Figure 13B:
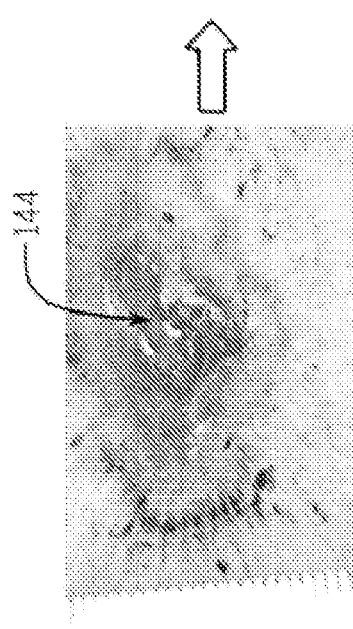
Figure 13C:
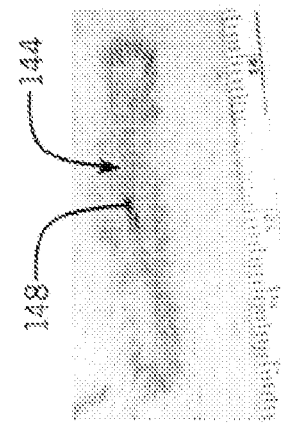
Figure 14A:
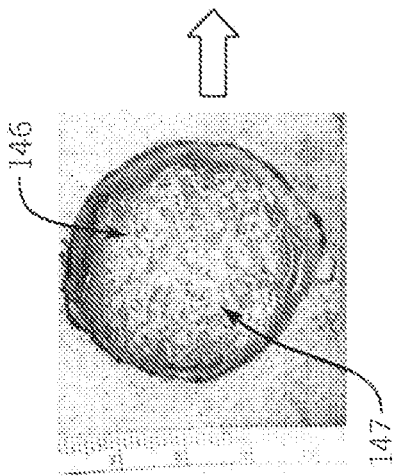
Figure 14B:
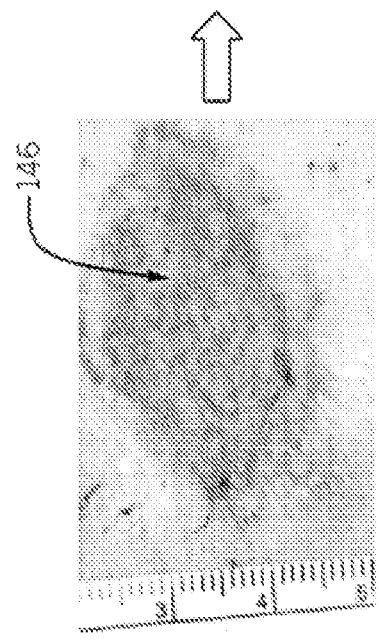
FIG. 14B illustrates the wound two weeks after time zero.
Figure 14C:
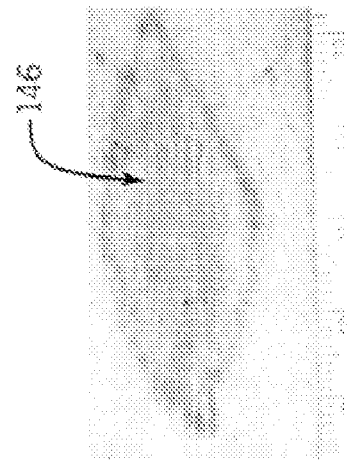
FIG. 14C illustrates the wound six weeks after time zero.

For example, FIGS. 13A-13O illustrate a typical secondary intention healing process of an untreated skin wound 144 at time zero, two weeks, and six weeks, respectively. FIGS. 14A-14C illustrate a healing process of a skin wound 146 treated with randomly oriented MTCs 147 at time zero, two weeks, and six weeks, respectively. As shown in FIG. 13C, after six weeks, the untreated wound 144 has slowly healed, mostly by contraction, with a portion 148 of the wound 144 still open. On the other hand, as shown in FIG. 14C, at six weeks, the wound 146 treated with randomly oriented MTCs is completed closed, healing faster than the untreated wound 144 and with less contraction.

Figure 15C:
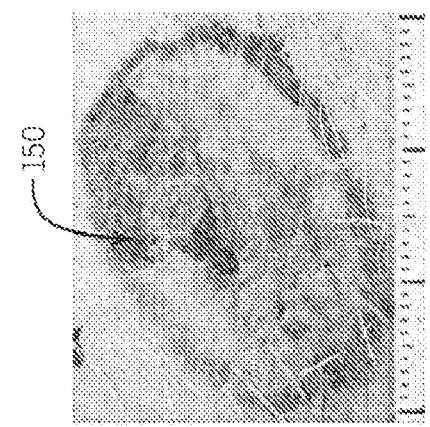
FIGS. 15A-15F illustrate top views of a wound healed by micro tissue grafts assembled in an epidermal-dermal orientation, where
Figure 15F:
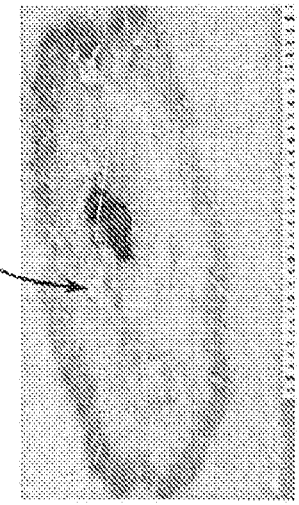
Figure 15B:
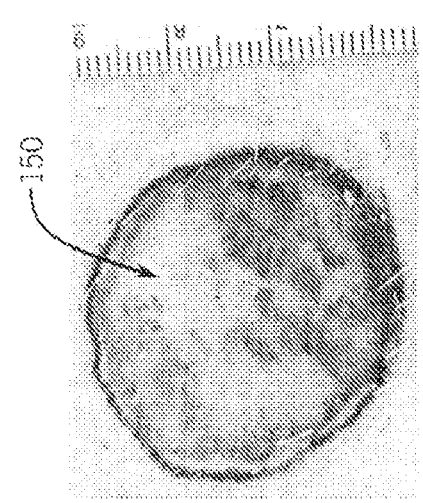
Figure 15E:
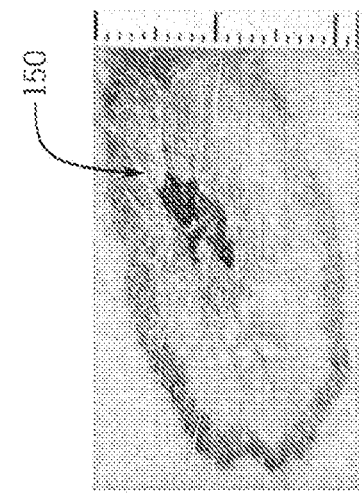
Figure 15A:
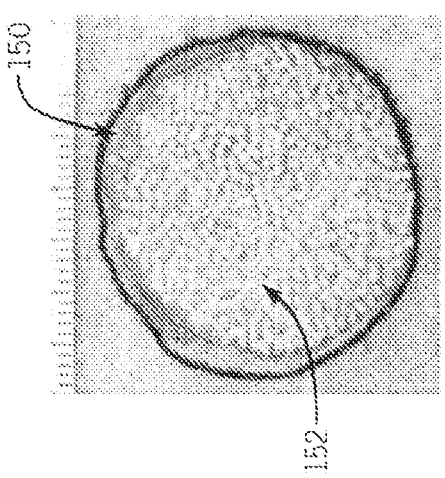
Figure 15D:
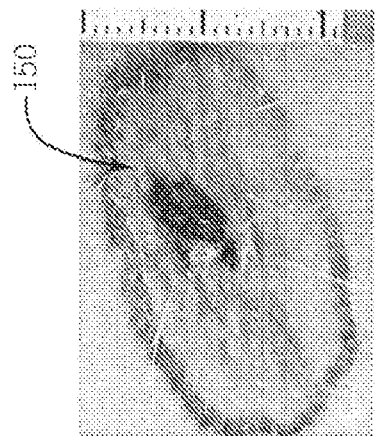

In comparison to randomly oriented MTCs, MTC constructs arranged in an epidermal-dermal orientation can provide faster healing time with less contractile response, and result in a healed wound that better matches normal tissue coloring and structure (e.g., that better matches an appearance and structure of the tissue that surrounds the recipient site). For example, FIGS. 15A-15F illustrate a healing process of a skin wound 150 at time zero, one week, three weeks, four weeks, six weeks, and eight weeks, respectively, treated using properly oriented MTCs 152 in accordance with the methods described above (e.g., using a solid construct of properly oriented MTCs 152). Generally, wounds reconstructed with properly oriented MTCs tend to appear more oval or round (for example, as shown in FIGS. 15D-15F), compared to wounds reconstructed with randomly oriented MTCs, which tend to be shaped with more pointed ends. The rounder appearance of properly oriented MTC wounds may indicate a less severe contractile response.

As another example, studies comparing collagen staining of untreated, random-MTC treated, and oriented-MTC treated skin wounds illustrate that oriented-MTC treated wounds, in accordance with systems and methods of the present disclosure, heal in a way that better matches normal tissue. For example, comparisons of collagen staining of untreated (that is secondary intention-healed wounds) and random-MTC treated wounds illustrate that the healed areas of both types of wounds were a distinctly different color than the surrounding normal tissue. Additionally, the random-MTC treated wounds had a more undulating dermoepidermal (DE) junction, more similar to normal skin, compared to wounds closed by secondary intention, which showed effacement of the DE junction (consistent with scarring). Such comparisons showed that, with secondary intention healing, the collagen structure of the wound was disrupted and the collagen fibers were thin and haphazardly organized. With randomly oriented MTCs, some collagen structure was seen, but was abnormal compared to the surrounding tissue.

However, in wounds treated with properly oriented MTCs, the DE junction appears much more like that of normal skin and dermal staining color (e.g., given by Herovici's stain) is much closer to normal skin, compared to wounds treated by random MTCs or secondary intention. Additionally, in wounds treated with properly oriented MTCs, collagen fibers are thicker, better match staining of normal collagen fibers, and are organized in a manner that is much closer to normal skin compared to random-MTC or secondary intention wounds.

In light of the above, small columns of full-thickness skin tissue can be harvested, with each donor wound being small enough to heal quickly by regeneration with minimal to no scarring. While such columns can be applied to wound beds randomly to accelerate wound healing, using tissue columns organized in a defined epidermal-dermal orientation can be advantageous by providing for more efficient cell and tissue growth and more faithful replication of normal tissue microanatomy. Furthermore, the above methods and systems for grafting and assembling MTCs are simple and nontoxic, using biocompatible supportive materials to form solid constructs that can be used as scalable building blocks capable of properly fitting a desired size and geometry of a recipient site.

The above methods and systems may be used in different wound healing applications, such as, but not limited to, burns, abrasions, and surgical wounds, or other grafting applications, such as, but not limited to, vitiligo. Additionally, while the above methods and systems have been described with respect to skin grafts, the principles described herein may applied to other tissue types as well. For example, the above methods and systems may be used with other types of tissue, such as, but not limited to, tissue of the liver, kidney, or heart, to provide micro tissue columns arranged in a desired orientation.

The present invention has been described in terms of one or more preferred embodiments, and it should be appreciated that many equivalents, alternatives, variations, and modifications, aside from those expressly stated, are possible and within the scope of the invention. Furthermore, the term "about" as used herein means a range of plus or minus 20% with respect to the specified value, more preferably plus or minus 10%, even more preferably plus or minus 5%, most preferably plus or minus 2%. In the alternative, as known in the art, the term "about" indicates a deviation, from the specified value, that is equal to half of a minimum increment of a measure available during the process of measurement of such value with a given measurement tool.

The invention claimed is:

1. A method for assembling a plurality of micro tissue grafts, the method comprising:
   a) harvesting the plurality of micro tissue grafts from a donor site;
   b) arranging the plurality of micro tissue grafts in a desired orientation, wherein step b) includes placing the plurality of micro tissue grafts in a solution and inducing the plurality of micro tissue grafts to organize in the desired orientation;
   c) forming a tissue construct containing the plurality of micro tissue grafts arranged in the desired orientation;
   d) applying the tissue construct to a recipient site; and
   further comprising applying a coating over a surface of the donor site so that an upper surface of each of the plurality of micro tissue grafts contains the coating.

2. The method of claim 1, wherein the coating is a hydrophobic coating; and wherein inducing the plurality of micro tissue grafts to organize in the desired orientation includes inducing the plurality of micro tissue grafts to organize in the desired orientation spontaneously due to hydrophobic properties of the coating within the solution.

3. The method of claim 1, wherein the coating is a magnetic coating; and wherein inducing the plurality of micro tissue grafts to organize in the desired orientation includes applying a magnet over the coating to induce the plurality of micro tissue grafts to organize in the desired orientation.

4. The method of claim 1, wherein inducing the plurality of micro tissue grafts to organize in the desired orientation includes controlling a flow of the micro tissue grafts in the solution.

5. The method of claim 4, wherein controlling the flow includes subjecting the solution to orbital motion.

6. The method of claim 1, wherein the tissue construct in step c) includes the plurality of micro tissue grafts arranged in the desired orientation within a supportive material.

7. The method of claim 6, wherein the supportive material is a biocompatible matrix.

8. The method of claim 1, wherein step c) includes maintaining the plurality of micro tissue grafts arranged in the desired orientation using one of a material and a tool in communication with an upper surface of the micro tissue grafts.

9. The method of claim 1, wherein the desired orientation is a substantially vertical epidermal-dermal orientation.

10. The method of claim 1 and further comprising repeating steps a) through c) to form a plurality of tissue constructs; and step d) includes applying the plurality of tissue constructs to the recipient site side-by-side.

11. The method of claim 1, wherein step c) includes placing the plurality of micro tissue grafts arranged in the desired orientation in the solution in liquid form; and inducing the solution to solidify to form the tissue construct.

12. A method for assembling a plurality of micro tissue grafts, the method comprising:
   a) harvesting the plurality of micro tissue grafts from a donor site;
   b) arranging the plurality of micro tissue grafts in a desired orientation, wherein step b) includes placing the plurality of micro tissue grafts in a solution and inducing the plurality of micro tissue grafts to organize in the desired orientation;
   c) forming a tissue construct containing the plurality of micro tissue grafts arranged in the desired orientation; and
   d) applying the tissue construct to a recipient site,
   wherein inducing the plurality of micro tissue grafts to organize in the desired orientation includes controlling a flow of the micro tissue grafts in the solution,
   wherein controlling the flow includes routing each of the plurality of micro tissue grafts through a respective fluid channel.

13. A method for assembling a plurality of micro tissue grafts, the method comprising:
   a) harvesting the plurality of micro tissue grafts from a donor site;
   b) arranging the plurality of micro tissue grafts in a desired orientation;
   c) forming a tissue construct containing the plurality of micro tissue grafts arranged in the desired orientation; and
   d) applying the tissue construct to a recipient site,
   wherein the tissue construct in step c) includes the plurality of micro tissue grafts arranged in the desired orientation within a supportive material, and wherein step c) includes rolling a strip of the supportive material and attaching the plurality of micro tissue grafts to the strip at spaced-apart intervals during rolling.

14. A method for assembling a plurality of micro tissue grafts, the method comprising:
   a) placing an apparatus over a donor site, the apparatus including an array of needles, a matrix with holes corresponding to each of the needles, and a mesh over the matrix;
   b) applying a vacuum over the apparatus to pull the plurality of micro tissue grafts through the array of needles and into the holes of the matrix, the mesh trapping the plurality of micro tissue grafts in the holes;
   c) removing the matrix from the mesh and the array of needles to form a tissue construct including the plurality of micro tissue grafts within the matrix; and
   d) applying the tissue construct to a recipient site.

15. The method of claim 14, wherein the matrix is a bilayer matrix, and step c) further includes removing one layer of the bilayer matrix to form the tissue construct including the plurality of micro tissue grafts within a remaining layer of the bilayer matrix.

16. The method of claim 14 and further comprising repeating steps a) through c) to form a plurality of tissue constructs; wherein step d) includes applying the plurality of tissue constructs to the recipient site side-by-side.

17. An apparatus for assembling a plurality of micro tissue grafts into a tissue construct, the apparatus comprising:
   an array of needles each sized to harvest a respective micro tissue graft from a donor site;
   a matrix positioned over the array of needles and including holes configured to receive the micro tissue grafts from the needles; and
   a mesh positioned over the matrix, the mesh sized to permit air to pass therethrough so that an applied vacuum pulls the micro tissue grafts through the needles into the matrix, the mesh further sized to contain the micro tissue grafts within the matrix.

18. The apparatus of claim 17, wherein the matrix includes a biocompatible material.

* * * * *

UNITED STATES PATENT AND TRADEMARK OFFICE
CERTIFICATE OF CORRECTION

Page 1 of 1

PATENT NO. : 11,065,031 B2
APPLICATION NO. : 16/344737
DATED : July 20, 2021
INVENTOR(S) : Richard Rox Anderson et al.

It is certified that error appears in the above-identified patent and that said Letters Patent is hereby corrected as shown below:

In the Specification

Column 4, Line 10, "14A-140C" should be --14A-14C--.

Column 11, Line 13, "FIG. 100" should be --FIG. 10C--.

Column 12, Line 15, "13A-130" should be --13A-13C--.

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*